US012611161B2

(12) United States Patent     (10) Patent No.:   US 12,611,161 B2

Barrettino et al.     (45) Date of Patent:     Apr. 28, 2026

(54) CARDIOVASCULAR MONITORING SYSTEM

(71) Applicant: ECOLE POLYTECHNIQUE FEDERALE DE LAUSANNE (EPFL), Lausanne (CH)

(72) Inventors: Diego Barrettino, Lugano (CH); Catherine Dehollain, Romanel-sur-Morges (CH); Kerim Ture, Renens (CH); Mustafa Besirli, Renens (CH); Marco Mattavelli, Chambesy (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 67 days.

(21) Appl. No.: 18/264,243

(22) PCT Filed: Feb. 1, 2022

(86) PCT No.: PCT/EP2022/052253
§ 371 (c)(1),
(2) Date: Aug. 3, 2023

(87) PCT Pub. No.: WO2022/167382
PCT Pub. Date: Aug. 11, 2022

(65) Prior Publication Data
US 2024/0115229 A1     Apr. 11, 2024

(30) Foreign Application Priority Data
Feb. 4, 2021    (EP) ..................................... 21155337

(51) Int. Cl.
   *A61B 8/06*       (2006.01)
   *A61B 8/00*       (2006.01)
   *A61B 90/00*      (2016.01)

(52) U.S. Cl.
   CPC ................ *A61B 8/065* (2013.01); *A61B 8/42* (2013.01); *A61B 8/4411* (2013.01);
                     (Continued)

(58) Field of Classification Search
   CPC .......... A61B 2560/0219; A61B 5/0031; A61B 5/0215; A61B 5/1076; A61B 5/6876; A61B 5/0883; A61B 5/029
   See application file for complete search history.

(56) References Cited

U.S. PATENT DOCUMENTS

| 3,661,148 A | 5/1972 | Kolin |
| 6,053,873 A | 4/2000 | Govari et al. |

(Continued)

FOREIGN PATENT DOCUMENTS

WO     2020260397 A1    12/2020

OTHER PUBLICATIONS

International Search Report for PCT/EP2022/052253 mailed Jul. 18, 2022, 7 pages.

(Continued)

*Primary Examiner* — Nyrobi Celestine

(74) *Attorney, Agent, or Firm* — Nixon & Vanderhye PC

(57) ABSTRACT

A cardiovascular monitoring system for measuring at least cardiac output comprises an implantable unit (2) configured for placement in a section of artery of a patient and a portable external unit (1) configured for mounting against or close to a patient's skin for bidirectional communication with the implantable unit. A cross-sectional area measurement sensor (8) includes at least one elastic conductive loop (15, 15a, 15b) and an electronic circuit (16) connected to the conductive loop configured to measure an inductance value of the conductive loop. At least one ultrasound transducer (7,11) is further configured to measure a velocity of blood flow based on a Doppler effect.

10 Claims, 8 Drawing Sheets

(52) U.S. Cl.

CPC .......... *A61B 8/4472* (2013.01); *A61B 8/4477* (2013.01); *A61B 8/4494* (2013.01); *A61B 8/488* (2013.01); *A61B 8/54* (2013.01); *A61B 8/56* (2013.01); *A61B 90/06* (2016.02); *A61B 2090/061* (2016.02); *A61B 2562/0247* (2013.01); *A61B 2562/0271* (2013.01); *A61B 2562/16* (2013.01)

(56) References Cited

U.S. PATENT DOCUMENTS

| | | | |
|---|---|---|---|
| 2003/0158584 A1 | 8/2003 | Cates et al. | |
| 2007/0088214 A1 | 4/2007 | Shuros et al. | |
| 2018/0177486 A1* | 6/2018 | Gifford, III | A61B 8/4227 |
| 2021/0038094 A1* | 2/2021 | Sweeney | A61F 2/86 |
| 2022/0240792 A1* | 8/2022 | Wetterling | A61B 5/02007 |
| 2022/0265157 A1* | 8/2022 | Charthad | A61B 8/488 |

OTHER PUBLICATIONS

Written Opinion of the ISA for PCT/EP2022/052253 mailed Jul. 18, 2022, 9 pages.

\* cited by examiner

The External Readout Unit

Chest Strap

12

1

The Implantable System

2

Pulmonary Artery

Pulmonary Trunk

Linear Fit

| Parameter | Value | Fixed | Error | R² |
|---|---|---|---|---|
| Inductance | | | | |
| Intercept | 144,0232 | ☐ | 0,62963 | 0,99661 |
| Slope | 1,28709 | ☐ | 0,02502 | |

Polynomial Fit

| Parameter | Value | Fixed | Error | R² |
|---|---|---|---|---|
| Inductance | | | | |
| Intercept | 127,38038 | ☐ | 0,56381 | 0,99997 |
| B1 | 2,64127 | | 0,04565 | |
| B2 | -0,02711 | | 9,12568E-4 | |

FIG. 7

Simulation:
- external ultrasonic transducer located at 10cm of the implanted ultrasonic transducer encapsulated in glass
- voltage amplitude10V at a frequency of 73kHz Result:
- voltage change in the implanted ultrasonic transducer of 15µV
- Doppler effect of blood flow of 50cm/s can be measured A: reference flow velocity = 50cm/s with emitter
Total Deformation 3
Type: Total Deformation
Frequency: 73616 Hz
Sweeping Phase: 0. °
Unit: m 1.9131e-9 Max
1.7053e-9
1.4976e-9
1.2899e-9
1.0821e-9
8.7442e-10
6.6669e-10
4.5895e-10
2.5122e-10
4.3491e-11 Min

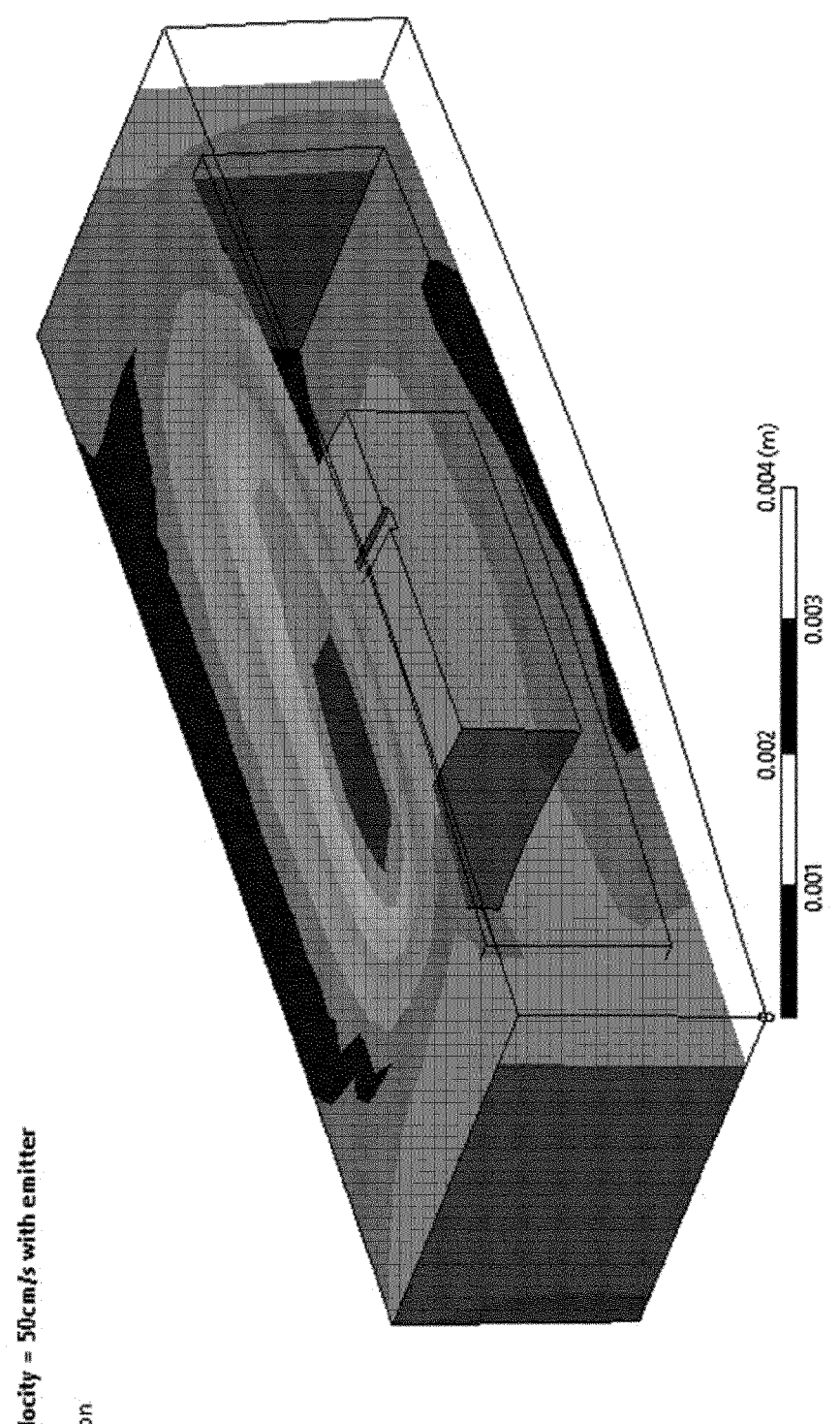

0.001      0.002      0.003      0.004 (m)

CARDIOVASCULAR MONITORING SYSTEM

CROSS-REFERENCE TO RELATED APPLICATIONS

This application is the U.S. national phase of International Application No. PCT/EP2022/052253 filed Feb. 1, 2022, which designated the U.S. and claims priority to EP 21155337.5 filed Feb. 4, 2021, the entire contents of each of which are hereby incorporated by reference.

FIELD OF THE INVENTION

This invention relates to a system with an implantable device and an external unit, for monitoring cardiovascular performance, including cardiac output.

BACKGROUND OF THE INVENTION

Heart failure (HF) disease occurs when the heart muscles cannot pump enough blood as needed by the body. HF is one of the most important issues faced by humankind in the 21st century as it affects around 26 million people worldwide, and it is a leading cause of morbidity and mortality. Prevalence of HF will continue to increase due to the prolonged lifespan of the general population. It is important to continuously monitor the heart activity, especially the cardiac output and pulmonary artery pressure (PAP), in order to adapt the treatments based on how the patients reacted to the prescribed drugs. Cardiac output is perhaps the strongest indicator of heart activity.

Continuous monitoring reduces the hospitalization rate and decreases the cost of the treatments. Monitoring of cardiovascular performance may however be important in many clinical and non-clinical environments for various purposes including detecting cardiovascular disease, determining the severity of the disease, monitoring the progression of the disease, guiding treatment and therapy, and for predicting the risk of cardiovascular failure.

In clinical environments, there are many non-invasive methods of measuring cardiac output, some of them based on ultrasound scanning of blood flows in a patient's heart or arteries, blood flow velocity being measured using the Doppler effect. This may be combined with blood pressure measurement sensors that are either implanted in an artery of the patient or that are non-invasive, for instance using a sphygmomanometer, or using optical sensors placed on the patient's skin. In many conventional devices, the available systems are either not well adapted for non-clinical environments, which precludes their use for continuous monitoring applications, or cannot detect cardiac output with a high accuracy that may reduce the quality of diagnosis or treatment, or of the prediction of possible cardiovascular failure. More accurate measurement of cardiac output would allow a more accurate evaluation of cardiac performance and related conditions such as heart failure.

Ultrasound monitoring of blood flow for measurement of cardiac output is for instance described in publications US2015351703, U.S. Pat. Nos. 10,206,651B2 and 7,798, 970B2. In vivo measurement of pressure and blood flow is also known and described, for instance in WO2007130628. In the latter system in view of the implanted pressure sensor device, a fairly accurate determination of blood pressure over time may be determined, however since the artery cross-section is not accurately measured or determined, the estimation of a blood flow rate, and accordingly of a cardiac output, is not accurate. Also, the measurement of the pressure may not form an accurate representation of blood flow, compared to the ultrasound Doppler effect techniques that measure a velocity of the blood flowing in a section of artery being observed. Of course, for invasive medical devices, the capacity, safety and reliability of the device is of paramount importance.

SUMMARY OF THE INVENTION

In view of the foregoing, an object of the invention is to provide a system for monitoring cardiovascular performance, including cardiac output, that is accurate, reliable and safe.

It is advantageous to provide a system for monitoring cardiovascular performance that may be used conveniently in clinical and non-clinical environments.

It is advantageous to provide a system for monitoring cardiovascular performance that has minimal discomfort for the patient.

It is advantageous to provide a system for monitoring or measuring cardiovascular performance, and particularly cardiac output, which may be performed substantially continuously over days, weeks or months, for a substantial portion of each day in a continuous manner if needed, and in a non-clinical environment, without reducing the patient's mobility.

Objects of this invention have been achieved by providing a cardiovascular monitoring system according to claim 1.

Disclosed herein is cardiovascular monitoring system for measuring cardiovascular parameters including at least cardiac output, comprising an implantable unit configured for placement in a section of artery of a patient, in particular a pulmonary artery, and a portable external unit configured for mounting against or close to a patient's skin for bidirectional communication with the implantable unit.

According to a first aspect of the invention, the implantable unit comprises a cross-sectional area (CSA) measurement sensor including at least one elastic conductive loop and an electronic circuit connected to the conductive loop configured to measure an inductance value of the conductive loop.

Measurement of the inductance value within the implantable sensor provides greater accuracy and reliability compared to a system using an external unit to create a magnetic field applied on an implanted conductive loop, such as disclosed in WO2020/260397.

According to a second aspect of the invention, the external unit and the implantable unit each comprise an ultrasound transducer configured for bidirectional communication between the external unit and implantable unit and for transmission of power from the external unit to the implantable unit.

The ultrasound transducer of the external unit is configured to transmit ultrasound excitation signals and at least one of said ultrasound transducers of the external unit or of the implantable unit is further configured to measure a velocity of blood flow based on a Doppler effect.

Combining the measurements of cross-sectional area and blood flow velocity as set forth in the present invention provides an accurate blood flow rate measurement. This is because the implantable sensor allows to provide measurements of the cross-sectional area and the blood flow velocity in a specific section of artery which can be combined to ensure an accurate measurement of blood flow rate since it takes into account the cross-sectional area at the point of measurement of the blood flow velocity.

In an advantageous embodiment, the CSA comprises at least two said elastic conductive loops, preferably arranged in substantially orthogonal planes.

In an advantageous embodiment, the ultrasound transducer of the external unit comprises a piezoelectric transducer array forming a plurality of transducer elements.

In an advantageous embodiment, the piezoelectric transducer array forming a plurality of transducer elements is in a concentric rings arrangement.

In an advantageous embodiment, the external unit comprises a plurality of ultrasound transducers arranged in a two dimensional pattern to cover a surface area larger than a single said ultrasound transducer.

In an advantageous embodiment, the external unit comprises a signal processing system comprising a controller, a frequency generator generating a reference frequency signal, and a mixer circuit portion connected to a measurement element of the ultrasound transducer and to said frequency generator for measuring a shift in frequency of the reflected ultrasound signals captured by said measurement element relative to said reference frequency signal.

In an advantageous embodiment, the implantable unit further comprises a pressure sensor, for instance in the form of a MEMS pressure sensor having a membrane or pressure sensing surface in communication with the external environment of the implantable unit.

In an advantageous embodiment, the implantable unit further comprises a temperature sensor in the electronic circuit of the implantable unit. In an advantageous embodiment, the temperature sensor comprises a CMOS-based temperature sensor.

In an advantageous embodiment, the implantable unit comprises a housing made of a biocompatible material at least at the outer surface thereof, encapsulating the ultrasound transducer, a circuit board and electronic circuit, and a pressure sensor. An opening may be provided in the housing for exposing a membrane of the pressure sensor.

In an advantageous embodiment, the implantable unit comprises an electronic circuit including a controller, sensor readouts connected to the controller, a serializer connected to the sensor readouts configured to output a serial bit stream from a parallel stream of bits output by the sensor readouts, and an uplink transmitter connected to the serializer and the ultrasound transducer for transmission of measurement data to the external unit.

In an advantageous embodiment, the implantable unit comprises an electronic circuit including a rectifier connected to the ultrasound transducer and a voltage regulator configured to generate a DC voltage supply $V_{supply}$ to the electronic circuit from ultrasound energy transmitted by the external unit and captured by the ultrasound transducer of the implantable unit.

Further objects and advantageous aspects of the invention will be apparent from the claims, and from the following detailed description and accompanying figures.

BRIEF DESCRIPTION OF THE DRAWINGS

The invention will now be described with reference to the accompanying drawings, which by way of example illustrate embodiments of the present invention and in which:

FIG. 7 is an illustration in 3D of a simulation of a Doppler effect measurement using an implanted ultrasonic transducer for measuring blood flow;

DETAILED DESCRIPTION OF EMBODIMENTS OF THE INVENTION

Figures 1, 2:
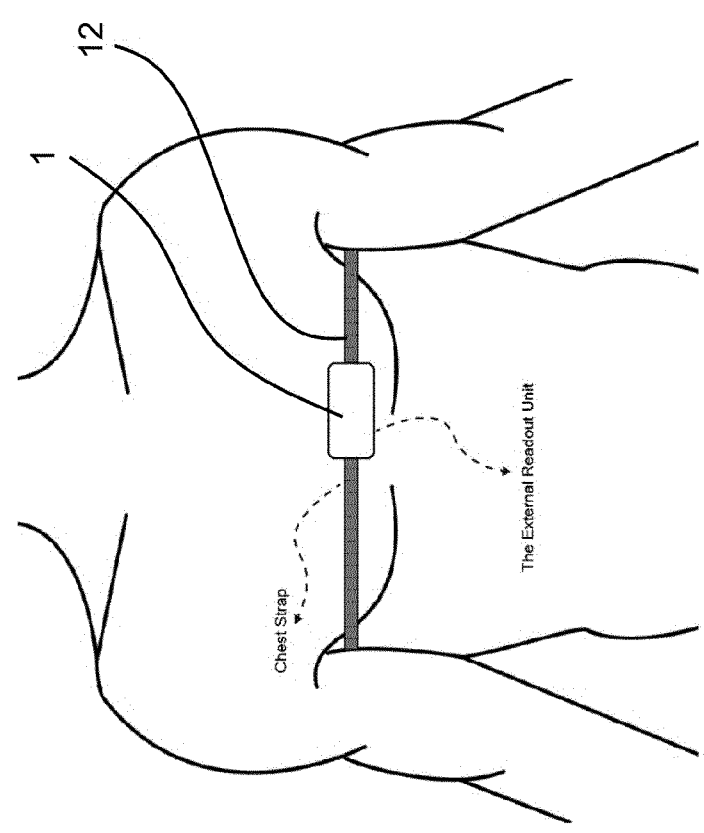
FIG. 1 is a schematic view of an implantable unit of a cardiovascular monitoring system mounted in a pulmonary artery of a patient's heart.
FIG. 2 is a schematic view of an external unit of a cardiovascular monitoring system according to an embodiment of the invention strapped to a patient's chest (over the position of the heart in which the implantable unit is mounted)
Figures 3A, 3B:
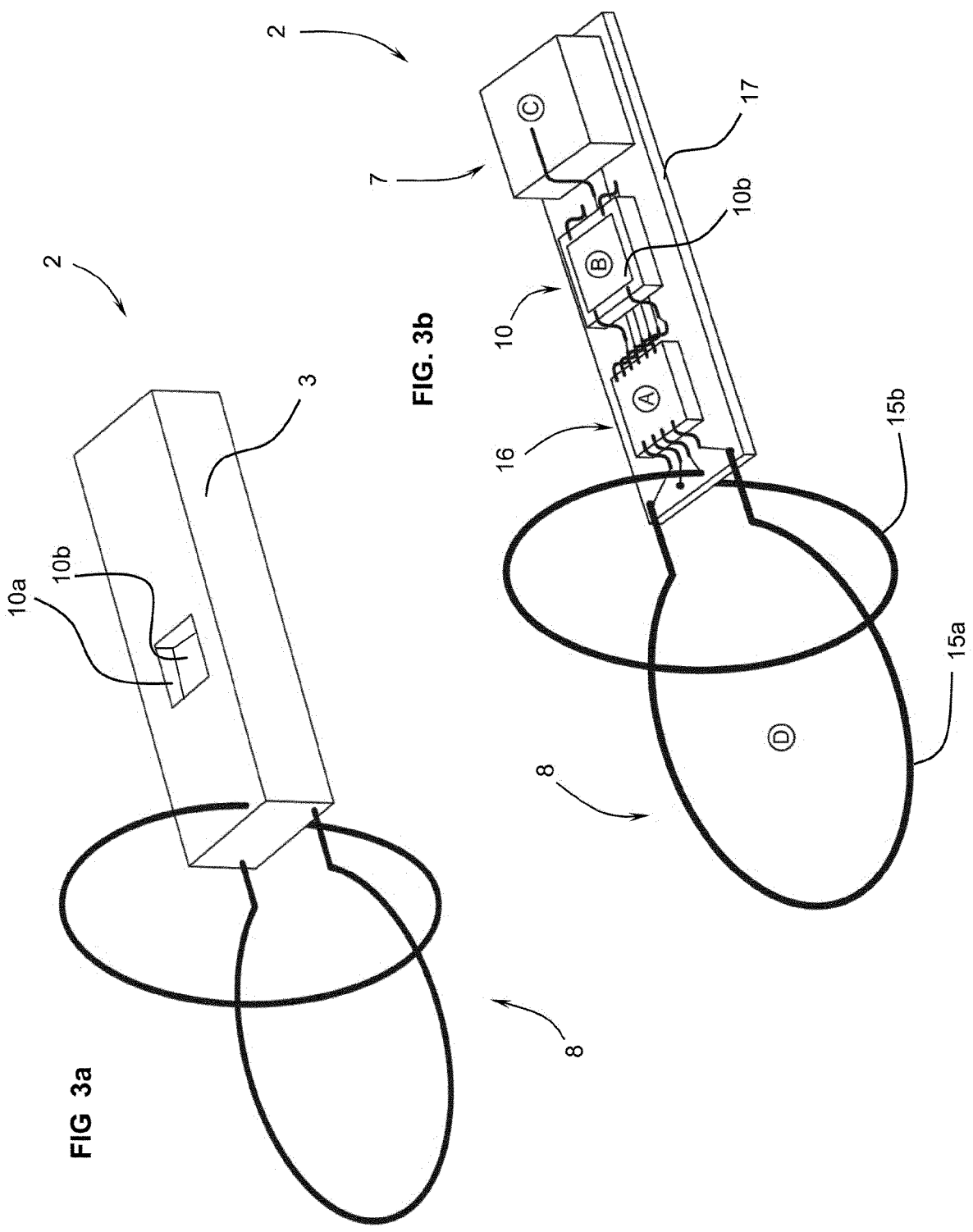
FIG. 3a is a schematic perspective view of an implantable unit of a cardiovascular monitoring system according to an embodiment of the invention.
FIG. 3b is a view similar to FIG. 3a with a housing of the unit removed to see the electronic circuit thereof.
Figure 4:
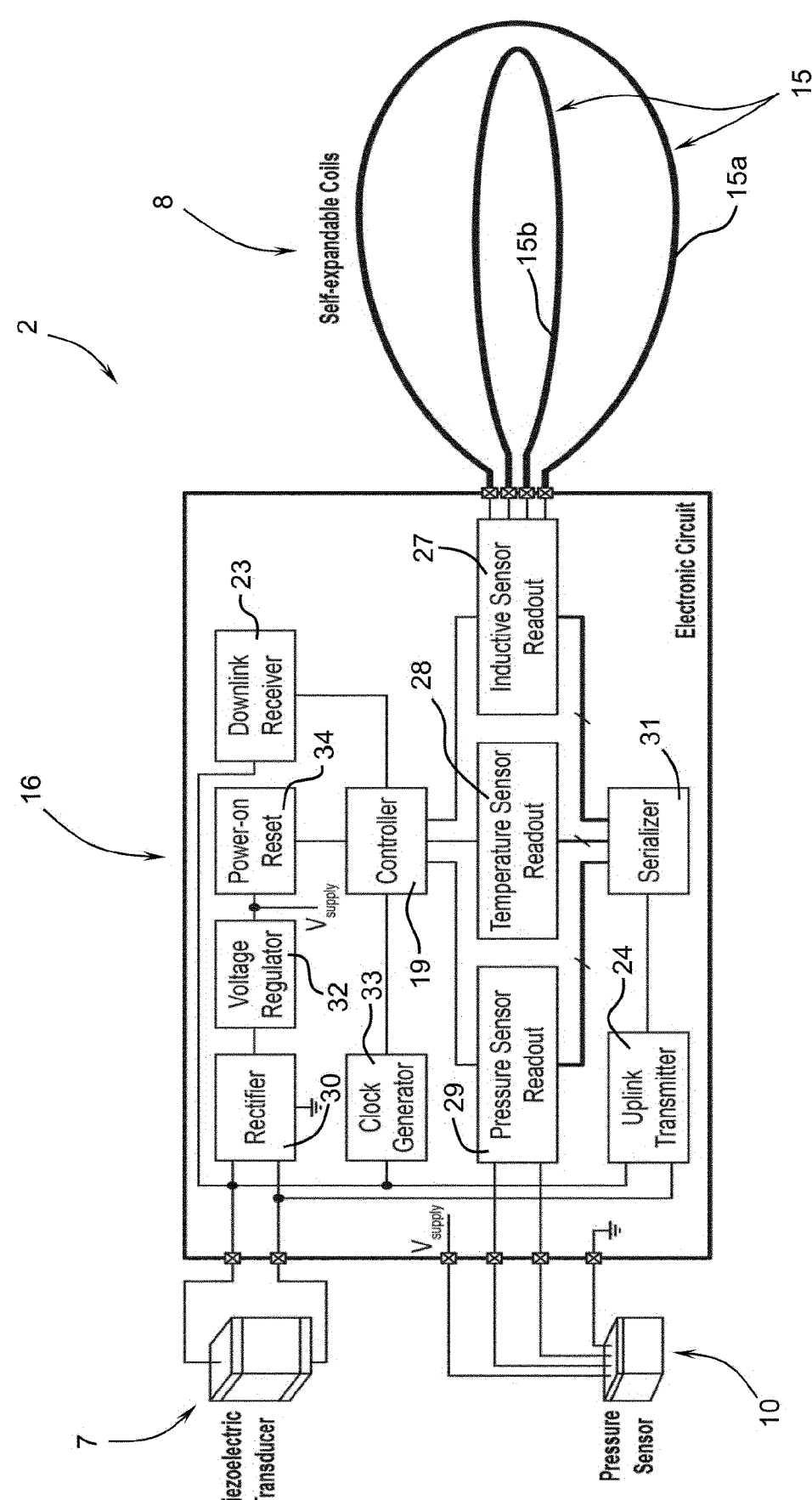
FIG. 4 is a schematic block diagram of the implantable unit, showing elements of an electronic circuit thereof according to an embodiment of the invention.

Referring to the figures, a cardiovascular monitoring system according to embodiments of the invention comprises an external unit 1 and an implantable unit 2. The external unit 1 is configured for mounting against or close to a patient's skin over a position in the body where the implantable unit is implanted. If the implantable unit 2 is mounted in the pulmonary artery of the patient at a position close to or in the patient's heart as illustrated in FIG. 1, then the patient would place the external unit 1 against the patient's chest over the position where the heart is located and in particular over the pulmonary artery where the implanted device is located, as illustrated in FIG. 2. The external unit 1 may be held on place with an elastic strap 12 that encircles the patient's thorax or may be held by means of an adhesive or by other means such as a clothing component. For intermittent monitoring, the external unit 1 may also be in the form of a hand held device that the patient or a health care practitioner may hold against the patient's chest (or any other position where the implantable unit is implanted) during the measurement procedure.

The external unit 1 provides power to the implantable unit 2 and establishes bidirectional communication with the implantable unit for the configuration of the implantable unit and for the reception of measurement data generated by the implantable unit.

The external unit 1 may be further configured to measure blood flow velocity in an artery of the patient.

The external unit 1 comprises an ultrasound transducer 11 and a signal processing system 34 for transmitting power and control signals to the implantable unit and for processing measurement signals, received from the implantable unit 2 and generated by the external unit. The external unit further comprises a power source 104, preferably an autonomous power source such as a battery, which may include a rechargeable battery and/or single use battery such as a lithium ion battery. The external unit may further comprise a wireless communications unit 13, for instance a wireless electromagnetic communications unit for data communication with an external computing device. The external computing device may be configured to collect and/or to process and/or to display cardiovascular measurement data received from the cardiovascular monitoring system.

The external unit 1 may further comprise a user interface (not illustrated) for providing information to the user and/or for allowing the user to control certain functions of the system. The user interface may include user input controls, such as user input buttons, that may for instance allow the user to control certain functions such as initiating a measurement cycle, transferring data, displaying measurement data or other information, or checking the status of the device. The user interface may further include status indicators such as a sound transducer and status lights. The user interface may further include a screen to display information on the measurement output such as pulmonary artery pressure, pulse rate, blood flow rate, cardiac output or other desired information. The measurement output may be displayed on a screen provided on the external unit that may be read directly therefrom by a healthcare practitioner or the patient. The external unit may also be configured without a screen or other interface elements such that information on cardiac performance may be transmitted via the wireless communications unit 13 and visualized on an external computing unit connection. The external unit may further be provided with a connector for wired data and/or power communication.

According to an aspect of the invention, the external unit 1 provides power to the implantable unit 2 and establishes bidirectional communication with the implantable unit by means of an ultrasound transducer 11. The ultrasound transducer may in particular comprise a piezoelectric transducer, however other ultrasound transducer technologies such as capacitive and electromagnetic transducer systems may be employed without departing from the scope of the invention. In an advantageous embodiment, the ultrasound transducer comprises a piezoelectric transducer array forming a plurality of transducer elements 90-99. Each of the transducer elements 90-99 may have one or more functions selected from power transmission, data transmission to the implantable unit, data reception from the implantable unit, and blood flow velocity measurement. Since power transmission represents the most energy that needs to be transmitted, preferably most of the transducer elements serve to transmit ultrasound power to the implantable unit 2, whereas one, two, or only a few more function as data communication elements, and one, two, or only a few more function as blood flow velocity measurement. The transducer elements may in an advantageous embodiment be in the form of concentric rings. The concentric ring elements may for instance be made of ceramic-polymer piezoelectric composite. In one embodiment of interest, the central element 99 may for instance be used for blood flow measurement signals, in particular to capture backscattered waves emitted by the external unit 1. Some or all of the other transducer elements 90-98 may be used for ultrasound power transmission. Some or all of the other transducer elements 90-98 may also be used for ultrasound data communication with the implantable unit 2. The concentric ring array structure advantageously provides flexibility on the focusing depth of the emitted ultrasound for the multiple functions of power, data and measurement signal transmission and reception.

Figure 5A:
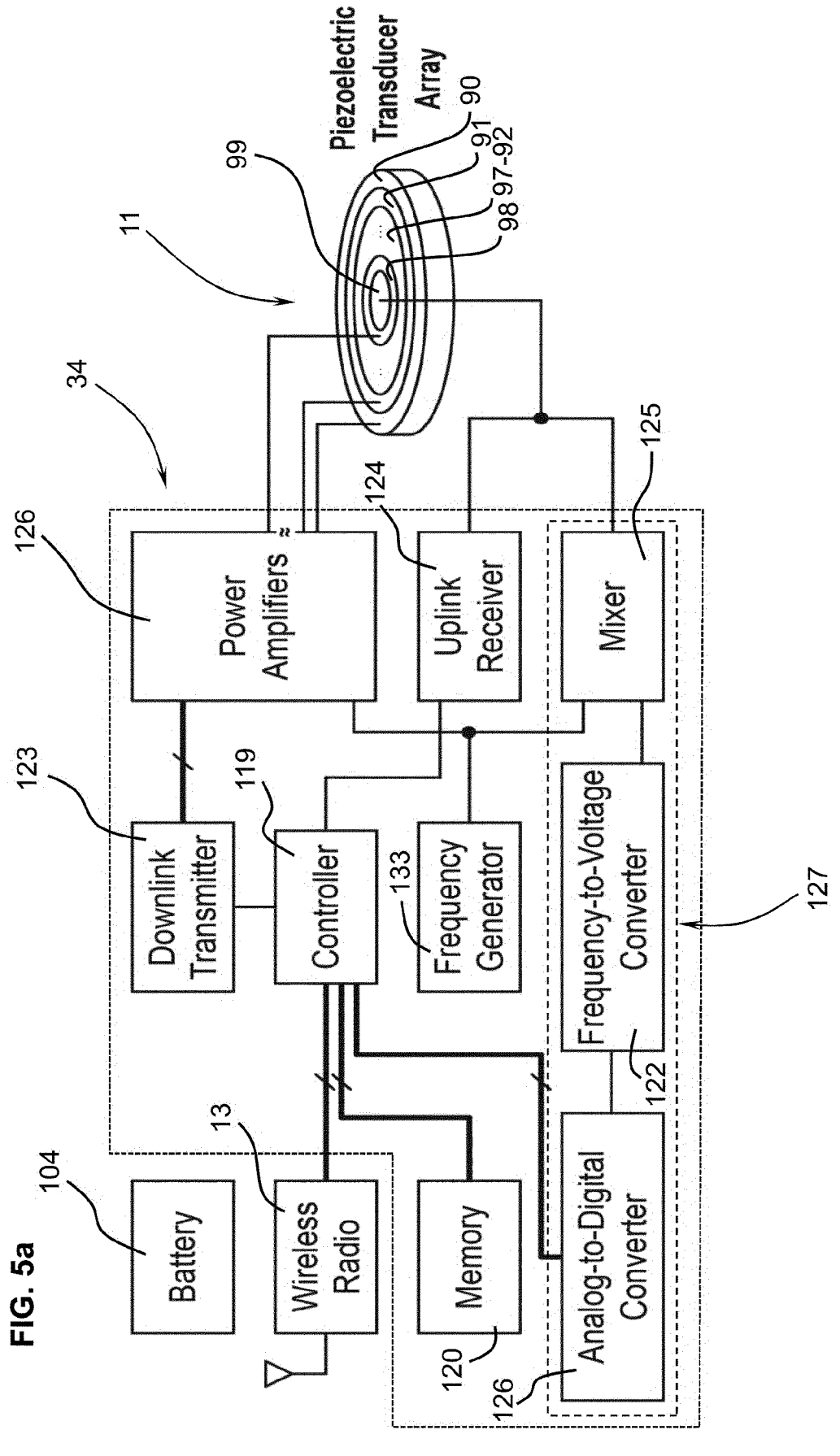
FIGS. 5a and 5b are schematic block diagrams of an electronic circuit of the external unit according to embodiments of the invention.
Figure 5B:
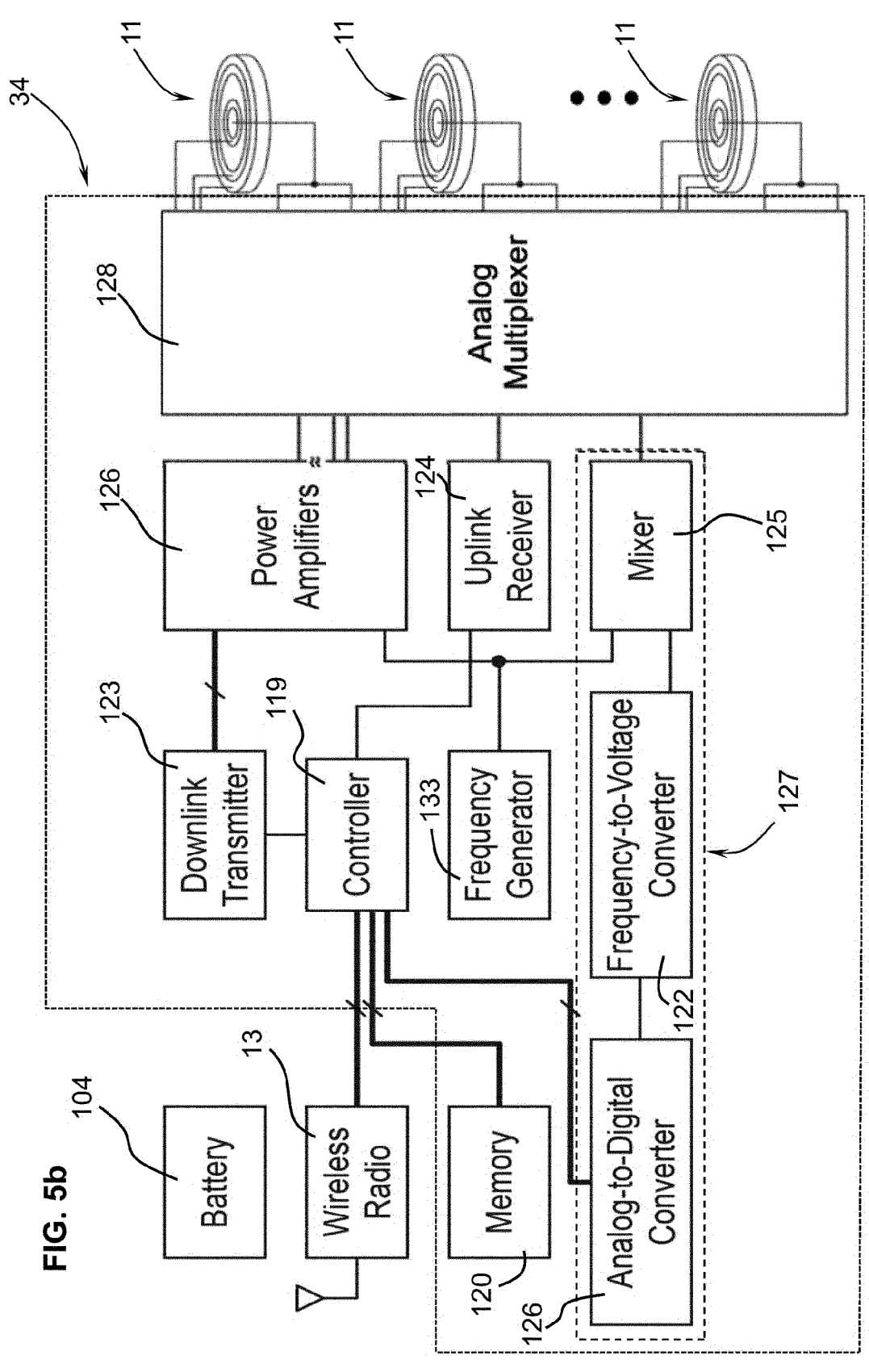

As schematically illustrated in FIG. 5b, the external unit may comprise a plurality of ultrasound transducers 11 arranged for instance in rows and columns (pattern not shown) or in other two dimensional patterns to cover a surface area larger than a single transducer. The plurality of ultrasound transducers are connected for instance via a multiplexer of the signal processing system 34 to the power amplifiers 126, uplink receiver 124 and mixer 125. The signal processing system 34 may advantageously be configured to drive only one of the ultrasound transducers 11, in particular the ultrasound transducer that has the strongest signal connection with the ultrasound transducer 7 of the implantable unit 2. This advantageously allows communication and power transmission between the external unit 1 and the implantable unit 2 to be optimized without changing the position of the external unit 1, by switching to the external ultrasound transducer 11 that provides the best communication with the implanted ultrasound transducer 7. Less correction of the position of the external unit is needed in use, and greater tolerance in the relative positioning of the external and implantable units is provided with this solution. Adjustment for depth is provided by the concentric ring arrangement of the transducer elements that allows to adjust for variations in the relative distance between the external and implantable units.

Depending on the implantable unit's depth in the body, the operation mode (e.g. ON/OFF) and the phase of the driving signal of each element in the piezoelectric transducer array may be determined by a controller 119 of the signal processing system 34. The driving signal may be applied by a downlink transmitter 123 of the signal processing system, connected to the controller 119, on the selected elements 90-98 of the transducer array, optionally via one or more power amplifiers 126 of the signal processing system to boost the amplitudes of the driving signals. The signal processing system 34 may further comprise a frequency generator 133 to control the frequency of the emitted ultrasound waves.

The signal processing system 34 of the external unit 1 may further comprise a memory 120 that may comprise a register for storing measurement data collected from the implantable unit 2 and measurement data generated by the external unit. The memory may also store device configuration data and other information useful or necessary for the functioning of the system.

The signal processing system 34 may further comprise an uplink receiver 124 for receiving measurement data. The uplink receiver 124 may in particular be configured to receive from the ultrasound transducer measurement signals generated by the reflected (backscattered) ultrasound signals, and to send the measurement data to the controller 119. The uplink receiver 124 demodulates the amplitude shifts or the phase shifts in the reflected waves which were created by the measurement data that changes the impedance of the implanted transducer.

The controller 119 may be part of the signal processing system 34 that may further comprise a blood flow measurement circuit section 127.

In an embodiment, the blood flow measurement section 127 comprises a mixer 125 connected to a measurement element 99 of the ultrasound transducer, a frequency-to-voltage converter 122, and an Analog-to-Digital Converter (ADC) 121. The mixer is also connected to the frequency generator 133 in order to measure a shift in the frequency of the reflected ultrasound signals captured by the measurement element 99 of the ultrasound transducer. The blood flow in the measured artery creates a Doppler shift between the frequencies of transmitted and received acoustic waves proportional to flow velocity. The mixer 125 calculates the frequency difference caused by the Doppler shift and it is converted to a voltage value by the frequency-to-voltage converter 122. The ADC 126 converts the analog signal from the frequency-to-voltage converter 122 into digital information that is sent to the controller 119 in order to calculate the blood flow velocity. In this first embodiment, the blood flow measurement is performed solely by the external unit 1.

In a second embodiment, the blood flow measurement is performed by the implantable unit 2 using ultrasound excitation signals transmitted by the external unit 1. FIG. 7 illustrates as simulation of the measurement for this second embodiment, in which the change of the blood flow is measured by voltage changes in of the ultrasound transducer 7 in the implantable unit 2 when it is excited by ultrasound signal from the ultrasound transducer 11 in the external unit 1.

The calculation in the controller 119 includes integrating the blood velocity for one heart beat time period and calculating a velocity time integral (VTI). A blood stroke volume (SV) is calculated by multiplying the VTI with a cross-sectional area (CSA) measurement value of the section of artery in which the implantable unit 2 is implanted:

$$SV_{\left[\frac{ml}{beat}\right]} = VTI_{\left[\frac{cm}{beat}\right]} \times CSA_{\left[cm^2\right]}$$

Heart beat rate (HR) measurement data may be obtained from the implantable unit 2, in particular from the measurement of blood pressure by a pressure sensor of the implantable unit and transmitted to the external unit, whereby the multiplication of SV and HR gives the cardiac output (CO).

$$CO_{\left[\frac{ml}{min}\right]} = SV_{\left[\frac{ml}{beat}\right]} \times HR_{\left[\frac{beats}{min}\right]}$$

The calculation of cardiac output may be performed in the controller 119 of the external unit 1, or may be performed in an external computing system by transferring the underlying measurement data (SV, HR, VTI, CSA). Measurement results received from the implantable unit 2 and the data calculated by the controller 119 of the external unit 1 may be stored in the memory 120 prior to intermittent transmission to the external computing system to decrease the working time of wireless communication module 13 and thus reduce its power consumption. The controller 119 may thus retrieve the stored information in the memory 120 and deliver it intermittently via the wireless communication module 13 to the external computing system, for calculation and/or display of cardiac measurement data, including cardiac output. More generally, various measurement and calculated data, for instance pressure, temperature, HR, SV, VTI, CSA and CO, may be sent by the external unit 1 to an external computing system which may include via a gateway to be uploaded to a cloud server.

The implantable unit 2 comprises a power system and a communication system. According to an aspect of the invention, the power system and communication system comprise a common ultrasound transducer 7 for the functions of the aforementioned systems.

According to an aspect of the invention, the power system of the ultrasound transducer 7 is configured to harvest power from ultrasound pressure waves transmitted by the external unit ultrasound transducer 11 towards the ultrasound transducer 7 of the implantable unit 2.

The implantable unit 2 according to another aspect of the invention further comprises a cross-sectional area (CSA) measurement sensor 8 for measuring a cross-sectional area of a section of artery in which the implantable unit is implanted.

The implantable unit may further comprise a pressure sensor 10, for instance in the form of a MEMS pressure sensor having a membrane or pressure sensing surface 10b in communication with the external environment of the implantable unit, for instance positioned within an opening 10a of a housing 3 of the implantable unit in contact with the blood in the artery surrounding the implantable unit. The pressure in the section of artery may thus be measured as a function of time, continuously or intermittently as required by the control of the implantable unit.

The implantable unit 2 further comprises a signal processing system 9. The signal processing system comprises an electronic circuit 16 that may be mounted on a circuit board 17. The circuit board 17 may form a support on which the electronic circuit 16, sensors 8, 10 and transducer 7 are mounted and interconnected. The electronic circuit 16 is connected to the sensors 8, 10 and ultrasound transducer 7.

The implantable unit may further comprise a temperature sensor which may be of a conventional type. In a preferred embodiment, the temperature sensor may for instance comprise a CMOS-based temperature sensor which exploits the temperature dependence of a gate-source voltage of a diode-connected MOS transistor and may advantageously be integrated in the electronic circuit 16.

A housing 3, having at least an outer surface thereof made of a biocompatible material, for instance of glass, encapsulates the electronic circuit, ultrasound transducer, pressure sensor and circuit board. A window or opening 10a may be provided for exposing a membrane 10b of the pressure sensor hermetically sealed to the window or opening.

The electronic circuit 16 may comprise a controller 19 connected to sensor readouts, in particular a pressure sensor readout 29, a temperature sensor readout 28 and an inductive sensor readout 27. The controller is connected through the sensor readouts 27, 28, 29 via a serializer 31 to an uplink transmitter 24 for transmission of sensor measurement data via the ultrasound transducer in the form of ultrasound signals to the external unit 1.

The controller is further connected to a clock generator 33 and a downlink receiver 23 connected to the ultrasound transducer 7 for processing data signals transmitted from the external unit as ultrasound signals and received by the ultrasound transducer 7 of the implantable unit 2.

The ultrasound transducer 7 is further connected to a rectifier 30 comprised in the electronic circuit for harvesting power of ultrasound power signals transmitted from the external unit 1 to the implantable unit 2 and captured by the ultrasound transducer 7, the rectifier being connected to a voltage regulator 32 to generate a voltage supply for the electronic circuit 16. The electronic circuit may further comprise a power-on reset circuit 34 connected to the controller and the voltage regulator for starting a measurement cycle when there is sufficient power. The electronic circuit 16 of the implantable unit may comprise further electronic components (not shown) for storing electrical energy such as on board battery or capacitors in order to supply power to the implantable unit for the data communication operations performed non concurrently with the power harvesting.

The CSA measurement sensor 8 according to an aspect of the invention comprises an inductive sensor comprising at least one conductive loop 15 (also named herein a "coil") having a width or diameter configured to engage the walls of the section of artery in which the implantable unit 2 is intended to be implanted, causing elastic deformation of the conductive loop 15. The at least one conductive loop 15 of the measurement sensor 8 may advantageously also perform the function of an anchoring element for the secure placement of the implantable unit 2. Ends of the inductive loop are connected to the electronic circuit 16, in particular the inductive sensor readout 27. The inductive sensor readout 27 is connected to the controller and configured to supply and measure current to the coil to determine the inductance value relative to a reference inductance value for a non-deformed coil. The amount of deformation of the conductive loop affects the inductance of the loop which can thus be correlated to the diameter of the artery section engaged by the inductive sensor. A dynamic variation in the diameter of the section of artery may also be used to measure cardiac blood flow pulses and thus heart rate (HR). The cross-sectional area can of course be determined from the diameter measurement of the artery assuming for instance a substantially cylindrical artery section shape. The inductive sensor may comprise a single conductive loop 15a, or may comprise two conductive loops 15a, 15b for measuring the diameter in different planes, preferably in essentially orthogonal planes. The orthogonal inductance measurements may also provide a redundant signal for safety, and/or may provide a more accurate measurement of the CSA, especially taking into account non-circular profiles of the section of artery in which the implantable sensor is implanted. The orthogonal loops also provide mechanical stability for the anchoring of the implantable unit 2 in the section of artery. Alternatively, one of the loops 15b may simply be a mechanical elastic loop for more stable anchoring of the implantable unit 2 in a section of artery.

The implantable unit 2 may be implanted using a catheter tool (not shown), whereby upon removal of the catheter tool, the elastically squeezed loop(s) of the CSA measurement sensor expand and engage the artery walls and hold the implantable system when the catheter tool is released from the catheter. The material used for the loops may include a conductive polymer or a metal, such as nitinol, elgiloy, stainless steel, cobalt chrome alloys, or any other suitable conductive materials with elastic properties sufficient to allow elastic compression for the range of diameters from the largest artery section (e.g. about 35 mm) down to the catheter insertion tool diameter (e.g. about 10 mm). There is also a tradeoff between better conductivity and less blood flow blockage for the material diameter used for forming coils and the number of coils. Preferably, the diameter of the conductive wire forming the loop is in a range of 0.5 mm to 2 mm, more preferably 0.5 mm to 1 mm.

The coils may advantageously be coated with biocompatible insulation materials such as polymide, polydimethylsiloxane (PDMS), Parylene-C or epoxy to electrically insulate the loops (which conduct a few milliamps of current in use) from the surrounding medium.

Acoustic power sent by the ultrasound transducer 11 of the external unit is received by the implantable unit's ultrasound transducer 7 which generates an alternating electrical current that is input into the rectifier 30 connected to the ultrasound transducer 7. The rectifier 30 converts the alternating current to DC (direct current) and outputs the DC current to the voltage regulator 32 to provide a constant supply voltage $V_{supply}$ to the electronic circuit 16. All the active circuits in the implantable unit 2 may be powered by $V_{supply}$ generated by the voltage regulator and the lowest potential (ground reference) in the electronic circuit may be generated by the rectifier. The incoming alternating current power signal from the ultrasound transducer's output is also connected to the clock generator 33 to generate a clock signal for the controller 19 and the sensor readout circuits 27, 28, 29.

Configuration parameters of the implantable unit 2 may be provided by amplitude modulation (typically minimum 15%) of the ultrasound power signal and may be demodulated by the downlink receiver 23. When the supply voltage $V_{supply}$ is high enough (for instance higher than 1.1V in an embodiment of this application), the Power-on-Reset circuit block 34 resets the controller 19 and a measurement cycle starts.

A first measurement in the implantable unit may be a pressure measurement. The pressure sensor 10 in an embodiment may for instance comprise or consist of a piezoresistive pressure sensor based on a Wheatstone bridge. The supply voltage $V_{supply}$ and the ground reference of the pressure sensor 10 are provided by the voltage regulator 32 and the rectifier 30 in the electronic circuit 16. The pressure sensor may comprise a differential output connected to the pressure sensor readout 29 which may comprise an instrumentation amplifier (IA) followed by an analog-to-digital converter (ADC).

Figure 8:
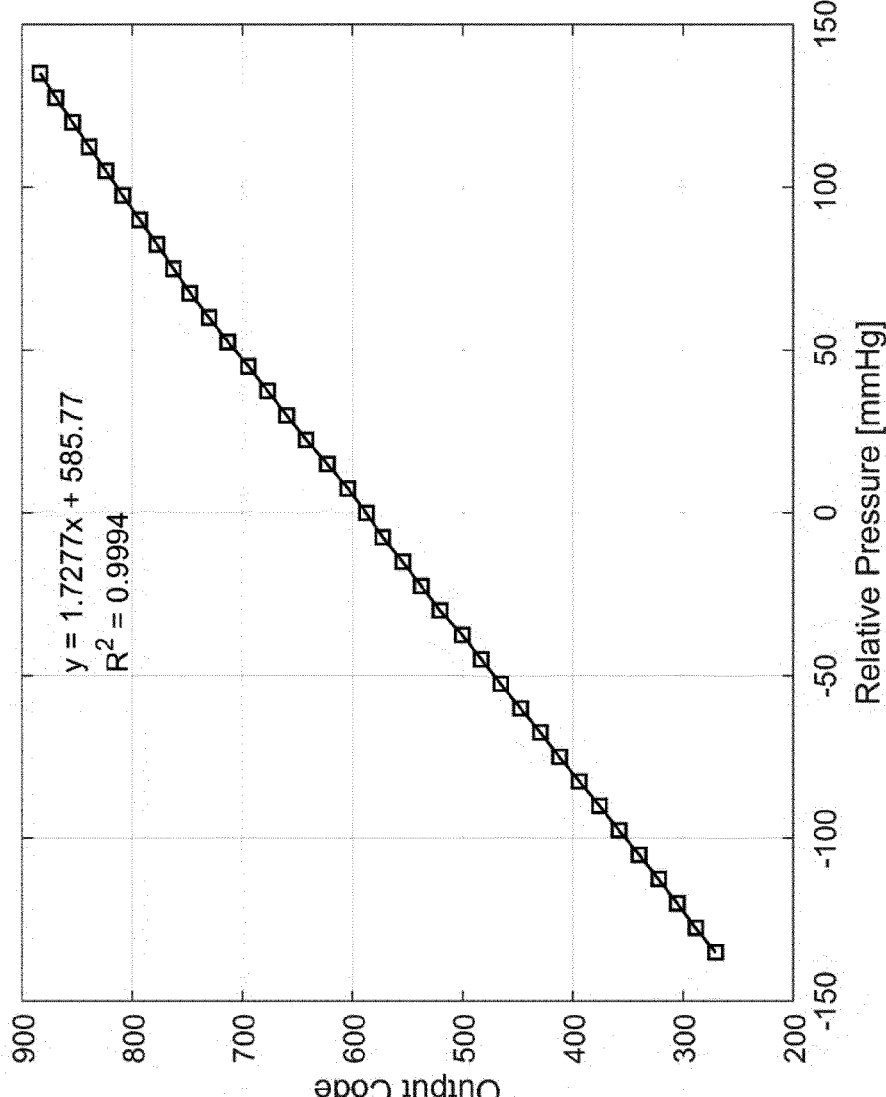
FIG. 8 is a plot of a measurement result of a pressure sensor readout of a cardiovascular monitoring system according to an embodiment of the invention.

The readout circuit 29 of the pressure sensor may for instance be designed with the following specifications:

a) In order to cover the extreme pressure limits, such as systolic PAP of pediatric patients, the measurement pressure range is selected to be from about 0 to about 135 mmHg. Since the atmospheric pressure decreases with increasing altitude, an additional margin in the negative pressure is also required. Thus, the overall pressure range with respect to the reference pressure (1 atm=760 mmHg) is selected to be from about −135 to 135 mmHg that allows calibration of the pressure sensor readout with respect to the ambient pressure. The overall pressure range is about 270 mmHg with a resolution preferably of between 0.4 to 0.5 mmHg, for instance about 0.45 mmHg. FIG. 8 illustrates an example of a measurement result of a MEMS pressure sensor readout relative to the reference pressure which is 1 atm (760 mmHg). The pressure range in this example is from −135 mmHg to 135 mmHg and the digital output code changes linearly from 271 to 884 that gives a resolution of 0.44 mmHg.

b) The system's bandwidth is set from about 0 to about 500 Hz, for instance from about 0 to about 400 Hz, to accurately detect fast peaks of systolic and diastolic pressure changes. The heart rate HR can be calculated by taking the time difference between two consecutive systolic or diastolic peaks.

In order to achieve a resolution of at least 0.5 mmHg, a 10-bit successive-approximation register (SAR) ADC may be implemented. In this way, systolic PA pressure can also be detected accurately in order to calculate the HR. The pressure sensor's readout circuit 29 may also include a programmable current source, which can be used to compensate for both the pressure sensor's offset voltage and atmospheric pressure.

The measured pressure is output by the ADC in the pressure sensor readout 29 to the serializer 31. The serializer outputs serial data on the measured pressure to the uplink transmitter 24 connected to the ultrasound transducer 7 for transfer by ultrasound signals to the external unit 1. Data serialization simplifies the transmission of signals for reliable information transfer via ultrasound, however within the scope of the invention non-serialized data transfer methods may also be used.

A second measurement in the implantable unit may be a temperature measurement, which may be performed separately or concurrently with other measurements, but preferably transmitted to the external unit non-concurrently from other measurements. In a preferred embodiment, the temperature measurement may for instance be performed after completion of the pressure measurement.

The temperature measurement is started by the controller 19. The temperature sensor readout 28 may comprise an instrumentation amplifier (IA) followed by an ADC. The temperature range may for instance be selected to be from 30° C. to 50° C., for instance from 32° C. to 45° C., and with a temperature resolution of between 0.02° C. and 0.2° C., preferably about 0.05° C., which may be achieved using an 8-bit or higher bit ADC. The output of the ADC in the temperature sensor readout 28 may be connected to the serializer 31. The transfer of temperature data to the external unit 1 may be performed in the same way as described above in relation to the transfer of pressure measurement data.

A third measurement in the implantable unit may be a CSA measurement, which may be performed separately or concurrently with other measurements, but preferably transmitted to the external unit non-concurrently from other measurements. In a preferred embodiment, the CSA measurement may for instance be performed after completion of the temperature measurement. The inductance measurement of the inductance coil(s) 15, 15a, 15b is started by the controller 19. The inductance of the self-expandable coils changes with the diameter of the section of artery where it is implanted.

The serializer circuit portion 31 may advantageously receive parallel output bits from the sensor readouts and converts the information to a serial bitstream, whereby the serializer may add identifier data for different measurements, for instance header bits as identification for different measurements.

In an advantageous embodiment, the uplink transmitter 24 is configured to modulate the input impedance seen from the ultrasonic transducer 7 for backscattering communication and transmission of measurement data to the external unit 1. The changes in the input impedance of the ultrasound transducer 7 create variations in the amplitude or in the phase of reflected ultrasound signals' originating from the external transducer. The modulated reflected acoustic waves can be detected by the ultrasound transducer 11 of the external unit 1 and converted to digital bits by the uplink receiver 124 in the external unit 1.

An example of materials and dimensions of an implantable unit 2 according to an embodiment of the invention is presented in the table below (it being understood that information in this table is for illustrative purposes only and many other per se known materials suitable for implantable medical devices, and other dimensions depending inter alia on the intended implant location, may be provided):

| | Material (example) | Dimensions (W × L × H) [mm³] (example) |
| --- | --- | --- |
| A: Electronic circuit: Integrated circuit (IC) | Silicon with Aluminum contacts | 2 × 2 × 0.3 |
| B: MEMS pressure sensor | Silicon with Aluminum contacts | 1.34 × 1.34 × 0.45 |
| C: Piezoelectric ultrasound transducer | Ceramic-polymer piezoelectric composite with gold contacts | 2 × 3.2 × 1 |
| D: Self-expandable induction coils | Nitinol | 120 mm (in length), 0.65 mm (in diameter) |
| E: Supporting substrate | Glass or printed circuit board (PCB) | 3 × 11 × 0.5 |
| Biocompatible housing | Glass | 3.5 × 12 × 2 |

One can observe for instance about an 8% difference in the inductance value between a 20 mm diameter artery and a 30 mm diameter artery using a same inductance coil. By building an oscillator with an elastically deformable inductance coil and a fixed-value capacitor, a change of the artery diameter may be detected by a change of the oscillator's frequency. This frequency can be compared with a reference frequency, for instance generated by the clock generator 33. The frequency comparison may for instance be carried out by an 8-bit or higher bit counter in the inductive sensor readout circuit portion 27. The 8- or higher bit output of the inductive sensor readout may also be connected to the serializer 31 to be transferred to the external unit 1, whereby the transfer of inductance data to the external unit 1 may be performed in the same way as described above in relation to the transfer of pressure measurement data. The computation of CSA based on the inductance measurements may be performed in the external unit 1 and/or in an external computing system. However, in embodiments of the invention, it is also possible to perform the CSA calculation within the implantable unit 2, or to perform CSA determination by referring to a look-up table stored in the electronic circuit 16 of the implantable unit 2, and transferring the CSA data to the external unit.

Figure 6:
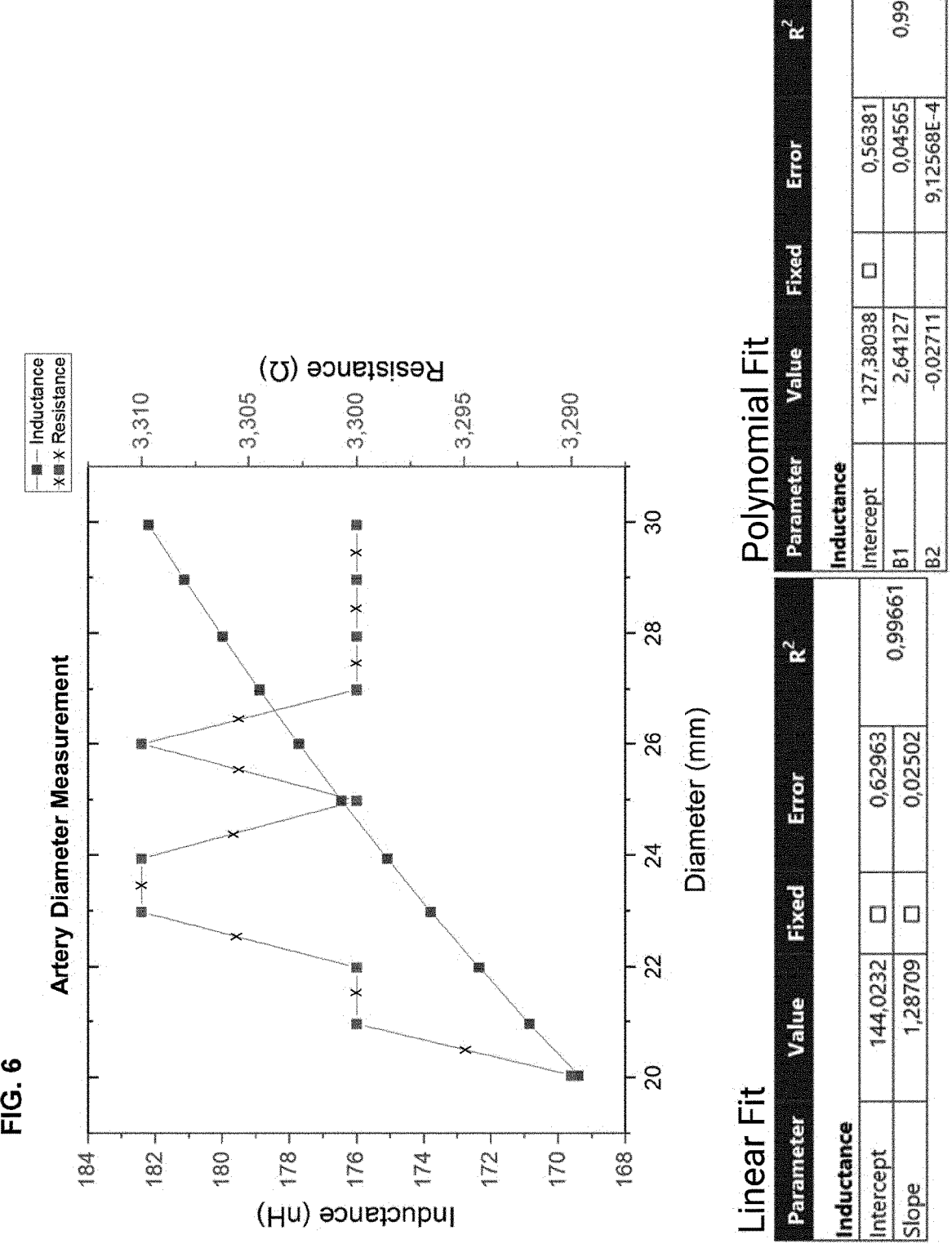
FIG. 6 is a plot of inductance vs diameter of an inductance sensor of the implantable unit for measuring a diameter of a patient's artery.

FIG. 6 shows some measurements of the inductance and resistance changes of an inductive coil 15 that is more or less elastically deformed when the artery diameter changes from 20 mm to 30 mm.

LIST OF FEATURE REFERENCES

Cardiovascular monitoring system
  External unit 1
    Ultrasound transducer 11
      Transducer array elements 90-99
    Fixing strap 12
    Signal processing system 34
      Controller 119
      Memory 120
      Blood flow measurement circuit section 127
        Frequency generator 133
        Mixer 125
        Frequency to Voltage Converter 122
        Analog to Digital Converter ADC 121
      Downlink transmitter 123
      Uplink receiver 124
      Power Amplifiers 126
      Multiplexer 128
    Wireless communication module 13
    Power Source 104
      Battery
  Implantable unit 2
    Housing 3
      Opening 10a
    Power System
    Communications system Ultrasound communications system
Ultrasound transducer 7
Piezoelectric transducer
Cross-sectional area (CSA) measurement sensor 8
Inductive sensor
Conductive loop(s) (coils) 15, 15a, 15b
Signal processing system 9
Circuit board 17
Electronic circuit 16
Controller 19
Downlink receiver 23
Uplink transmitter 24
Inductive sensor Readout 27
Temperature Sensor Readout 28
Pressure Sensor Readout 29
Rectifier 30
Serializer 31
Voltage Regulator 32
Clock generator 33
Power-on reset 34
Pressure Sensor 10
MEMS pressure sensor
Temperature sensor

The invention claimed is:

1. A cardiovascular monitoring system for measuring cardiovascular parameters including at least cardiac output, the cardiovascular monitoring system comprising:
an implantable unit configured for placement in a section of an artery of a patient; and
a portable external unit configured for mounting against, or close to, skin of the patient for bidirectional communication with the implantable unit, wherein
the portable external unit and the implantable unit each include an ultrasound transducer configured for bidirectional communication between the portable external unit and implantable unit and configured for transmission of power from the portable external unit to the implantable unit,
the implantable unit comprises a cross-sectional area (CSA) measurement sensor including at least two elastic conductive loops orthogonal to each other and an electronic circuit connected to the at least two elastic conductive loops and configured to measure an inductance value of the at least two elastic conductive loops to compute the CSA of the artery,
at least one of the ultrasound transducers is further configured to measure a velocity of blood flow based on a Doppler effect, and
the portable external unit is further configured to measure cardiovascular parameters including at least cardiac output based on the computed CSA and the measured velocity of blood flow of the artery.

2. The system according to claim 1, wherein the ultrasound transducer of the portable external unit is configured to transmit ultrasound excitation signals for measuring the velocity of blood flow based on the Doppler effect.

3. The system according to claim 1, wherein the ultrasound transducer of the portable external unit comprises a piezoelectric transducer array forming a plurality of transducer elements, and the plurality of transducer elements are in a concentric rings arrangement.

4. The system according to claim 1, wherein the portable external unit comprises a plurality of ultrasound transducers arranged in a two dimensional pattern to cover a surface area larger than a single ultrasound transducer.

5. The system according to claim 1, wherein the portable external unit comprises a signal processing system comprising:
a controller;
a frequency generator configured to generate a reference frequency signal; and
a mixer circuit portion connected to a measurement element of the ultrasound transducer and to the frequency generator and configured to measure a shift in frequency of the reflected ultrasound signals captured by the measurement element relative to the reference frequency signal.

6. The system according to claim 1, wherein the implantable unit further comprises a micro-electromechanical systems (MEMS) pressure sensor having a membrane or pressure sensing surface in communication with an external environment of the implantable unit.

7. The system according to claim 1, wherein the implantable unit further comprises a complementary metal-oxide semiconductor (CMOS)-based temperature sensor.

8. The system according to claim 1, wherein
the implantable unit comprises a housing made of a biocompatible material, at least at the outer surface thereof, and encapsulating the ultrasound transducer, a circuit board and electronic circuit, and a pressure sensor, and
the housing includes an opening for exposing a membrane of the pressure sensor.

9. The system according to claim 1, wherein the implantable unit comprises;
an electronic circuit including a controller;
sensor readouts connected to the controller;
a serializer connected to the sensor readouts and configured to output a serial bit stream from a parallel stream of bits output by the sensor readouts; and
an uplink transmitter connected to the serializer and the ultrasound transducer for transmission of measurement data to the portable external unit.

10. The system according to claim 1, wherein the implantable unit comprises:
an electronic circuit including a rectifier connected to the ultrasound transducer, and a voltage regulator configured to generate a direct current (DC) voltage supply $V_{supply}$ to the electronic circuit from ultrasound energy transmitted by the portable external unit and captured by the ultrasound transducer of the implantable unit.

* * * * *